United States Patent [19]

Navot

[11] Patent Number: 5,091,170

[45] Date of Patent: Feb. 25, 1992

[54] FERTILITY PREDICTION BY USE OF CLOMIPHENE CHALLENGE TEST

[76] Inventor: Daniel Navot, Virginia Beach, Va. 23464

[21] Appl. No.: 334,780

[22] Filed: Apr. 6, 1989

Related U.S. Application Data

[63] Continuation of Ser. No. 26,879, Mar. 17, 1987, abandoned.

[51] Int. Cl.$^5$ .............................................. A61K 49/00
[52] U.S. Cl. ........................................ 424/9; 436/65; 436/811; 436/906
[58] Field of Search .................. 436/501, 536, 65, 87, 436/811, 906; 530/387, 389; 424/9

[56] References Cited

U.S. PATENT DOCUMENTS

| | | | |
|---|---|---|---|
| 3,826,616 | 7/1974 | Laing | 23/230 |
| 4,278,668 | 7/1981 | Gueritee | 260/397.5 X |
| 4,339,434 | 7/1982 | Ericsson | 424/105 |
| 4,514,505 | 4/1985 | Caufield et al. | 436/548 X |

OTHER PUBLICATIONS

Baier, H., et al., "Effect of Clomiphene on Plasma FSH-Activity"; Chem. Abst. 70, p. 50, #103396h (1969).

Schally, A.V., et al., "Alteration of LH & FSH Release in Rats Treated With Clomiphene", Chem. Abst. 73, p. 53, #95043k (1970).

Giustina, G., et al., "Clomiphene-induced Modifications of Plasma LH. . . ", Chem. Abst., 76, p. 60, #135965h, (1972).

Terakawa et al.,-Chem. Abst. vol. 103 (1985) p. 17137t.
Badawi et al.-Chem, Abst. vol. 102 (1985) p. 40276a.

*Primary Examiner*—Sam Rosen
*Attorney, Agent, or Firm*—Stephan P. Williams

[57] ABSTRACT

The fertility of females, especially human females can be predicted by use of a clomiphene challenge test. The test is based upon comparison of follicle stimulating hormone and/or luteinizing hormone levels in urine or blood samples at two points in the menstrual cycle. The first test is performed on days 2-3 of the cycle. Clomiphene, and most preferably clomiphene in the form of clomiphene citrate, in a dosage of about 100 mg/day, is then administered, preferably on days 5-9. The second test is conducted on days 9-10. The test results are most conveniently compared by colorimetric methods involving monoclonal antibody reactions with follicle stimulating hormone and/or luteininizing hormone.

21 Claims, No Drawings

FERTILITY PREDICTION BY USE OF CLOMIPHENE CHALLENGE TEST

This application is a continuation of application Ser. No. 026,879, filed Mar. 17, 1987, now abandoned.

FIELD OF THE INVENTION

The present invention generally relates to methods for predicting female fertility. More particularly this invention relates to methods of predicting human female fertility based upon chemical tests for detecting the levels of follicle stimulating hormone or luteinizing hormone in the female's urine or blood.

BACKGROUND OF THE INVENTION

The fertility processes which occur in females, especially in human females, are highly complex, and continuing efforts are being made in this area to more fully understand these processes so as to facilitate the development of improved techniques for predicting and treating fertility problems as well as for providing more effective and reliable birth control methods. A number of drugs have been employed to treat infertility. Clomiphene citrate is one such drug. However, in the fertility problem area, there still is an acute need for improved methods for studying, as opposed to treating, women who wish to conceive but are unable to do so. For example, a woman seeking a career outside the home may consider postponing childbearing until her thirties, and a prognosticator of fecundity would be of special value to her. It might guide her decisions regarding pregnancy attempts and contraception. It also would aid the physician in clinical decisions regarding infertility workup or therapy. Moreover, this need extends to women experiencing other difficulties such as menstrual cycle variations and other problems associated with the female child bearing organs. However, for the apparently healthy, regularly menstruating woman, age is presently the only widely accepted parameter of fertility potential. Demographic studies indicate that fertility peaks during the early twenties, decreases noticeably after 30 years of age and markedly after 35 years. However, because of individual variations, age by itself is an inaccurate parameter, and arbitrary limits based on age alone can influence treatment decisions in a number of patients.

In the birth control area, there is also an acute need for improved birth control methods which are not only effective in preventing conception but also have a reduced incidence of adverse physical side effects. There are a wide variety of birth control methods available, but these are often unacceptable due to the fact that they are unreliable (i.e., prevention of conception is not assured), or for medical reasons, or on religious grounds. One example of a birth control method which is unreliable is the so-called "rhythm" method, which is based on the fact that the woman is not fertile, i.e., ovulation has not occurred or is not about to occur, during a certain period in her menstrual cycle. The major disadvantage associated with this method is that, while the time period from when ovulation naturally occurs to the next succeeding menstrual period is essentially fixed in all women, the time period between the beginning of a menstrual period and the next ovulation can vary considerably depending of the particular woman concerned. It is during the time period between the beginning of a menstrual period and the onset of the next succeeding ovulation that sexual intercourse can occur without conception occurring since during this period the female ovum has not yet been produced by the woman. However, significant risks do exist with the "rhythm" method since, even if the woman has not ovulated at the time of sexual intercourse, ovulation occurring one or two days thereafter can result in conception since the life span of male sperm in the vagina can be as long as one to two days, and sometimes longer.

Some methods do exist for determining when a woman is about to ovulate but these are inconvenient and difficult to interpret. One such method requires the woman to take her temperature every morning and to plot this on a graph. From the shape of the graph, it is possible to see when ovulation has actually occurred, but the major problems associated with this method is that fluctuations in body temperature can occur for many reasons other than the ovulation process.

It is also well known to this art that a surge in the level of human luteinizing hormone (hLH or HL) takes place about 34 hours prior to ovulation. It takes place according to considerations which can begin by first noting that the normal human menstrual cycle is divided into the follicular phase, ovulation, and the luteal phase. Normal hormonal control during the follicular phase produces maturation of the primary ovarian follicle. Human luteinizing hormone and human follicle stimulating hormone (hFSH or FSH) are known to have a sensitizing effect upon the primary ovarian follicle. These hormones act in concert to stimulate estrogen synthesis. It is also known that estrogen and hFSH achieve their sensitizing effects by inducing expression of gonadotropin receptors in preparation for ovulation. Estrogen in turn acts on the hypothalamus to control pituitary secretion of gonadotropins. Estrogen reaches a peak one to two days prior to ovulation. This peak in turn induces a positive feedback response in the anterior pituitary to hypothalamic gonadotropin releasing hormone. During this peak period, estrogen levels decrease while progesterone levels start to increase and thereby stimulate the release of high levels of hLH. This surge in the hLH level reaches peaks which are usually two to three times the preceding basal concentrations. This hLH surge in turn induces a rupture of the primary ovarian follicle and the resulting release of a mature oocyte. This phenomenon is generally referred to as "ovulation". Thereafter, hLH promotes luteinization and formation of the corpus luteum. This is followed by a decrease in the hLH level to baseline levels within two days in response to the peaking progesterone levels which serve to initiate the luteal phase which lasts about 14 days. In the absence of fertilization of the oocyte, a new follicle begins the selection procedure for maturation in the next menstrual cycle.

The methods for detecting the hLH surge have also improved in recent times. Before the development of immunoassays, analyses of hLH in urine was obtained by bioassay techniques. However, the clinical utility of these methods was limited; they had relatively low sensitivity and frequently required that urine extracts be tested. In the mid 1960's however, the introduction of radioimmunoassay for hLH provided a new tool for quantitating low levels hLH in urine or serum. The later introduction of enzyme immunoassays for hLH offered the further advantage of good sensitivity without the use of radioisotopes. Nonetheless, there still exists a need for improved methods for evaluating fertility in woman so that fertility problems can be alleviated or so that appropriate birth control methods can be selected. Moreover, the diagnosis of infertility problems is still hampered by the fact that prediction of ovulation does not in and of itself give any information as to whether or not the oocyte which is about to be released is one that is fecund.

Thus even though it is well known that the detection of the hLH surge can act as an important tool in the detection of ovulation since the onset of the hLH surge precedes ovulation by about 34 hours; and even though it is also known that peak hLH levels occur several hours later in urine than in serum with the onset of the surge in urine being about 30 hours before ovulation it has not been heretofore appreciated that differences in hLH and/or hFSH levels before and after ovulation could be used in a diagnostic test aimed at determining whether or not the female is releasing fecund oocytes.

SUMMARY OF THE INVENTION

The disclosed clomiphene challenge test can be utilized to prospectively assess future fertility potential in women, especially in women greater than 35 years of age with unexplained infertility. The test has four basic steps. A baseline hormone (most preferably FSH and/or LH) level is established; clomiphene is administered; a response hormone level is established; and the response level of the subject hormone is compared to its baseline level. The baseline period hormone level is preferably established on days 2-3. The response period level is preferably established on days 9-11. The human follicle-stimulating hormone (hFSH) and/or, human luteinizing hormone (hLH) levels are measured before and after administration of from about 50 mg to about 150 mg/per day of clomiphene between the baseline period and the response period. The clomiphene can be any clomiphene salt in any pharmaceutically acceptable carrier. However, in the most preferred embodiment of this invention, clomiphene is administered in the form of clomiphene citrate tablets. It can be administered between days 2 and day 9 of the menstrual cycle. However, daily administration on days 5,6,7,8 and 9 is a highly preferred administration procedure and dosages of about 100 mg/day of clomipheene citrate, in the form of clomiphene tablets, administered at the same time daily, is the most preferred administration procedure.

DESCRIPTION OF THE INVENTION

The disclosed clomiphene challenge test can be performed upon urine and/or blood samples. However, for reasons of simplicity, urine is the preferred sample source. Urinary or serum FSH or LH each can be measured in a number of known semiquantitative fashions. The tests can also be based o combined FSH and LH levels. Test for FSH alone are, however, a preferred method of conducting the test. Again for reasons of simplicity, colorimetric tests are preferred to other test procedures which could include other, less preferred test procedures such as, for example, radioimmunoassay or pathological tests. Most preferably, the colorimetric tests employed are those based upon color reactions of monoclonal antibody-based, enzyme immunoassay tests. Such colorimetric test results can be interpreted by the woman with the aid of color charts which are preferably made a part of a test kit.

For example, semiquantitative tests of human luteinizing hormone (hLH) in urine can be made by comparing certain color reactions which can be associated with a monoclonal antibody/hLH reaction. One such color reaction is described in a publication by Monoclonal Antibodies, Inc., entitled, "Ovustick TM Urine hLH Kit" (1984) and said publication is incorporated by reference into this patent application. Generally, it discloses that human luteinizing hormone is a glycoprotein hormone comprised of two noncovalently bound polypeptide subunits, designated alpha and beta units, having carbohydrate side chains. The amino acid sequence of alpha-hLH is essentially the same as that of human follicle-stimulating hormone. It has been established that the beta subunit of hLH is responsible for the biological and immunochemical specificity of this particular hormone.

Hence an hLH test kit normally used to chart ovulation could also be used as the test method to practice the herein disclosed clomiphene challenge test. Preferably it will be in the form of a visually determinable, enzyme immunoassay that incorporates the advantages of monoclonal antibody technology. Such antibodies offer the great advantage of controlled specificity and affinity. They will provide consistent assay performance since they enter into a specifically determined color reaction whose results can be compared by simple color comparison charts. Hence, tests utilizing monoclonal antibodies in semiquantitative, two-site, enzyme linked immunospecific assays are most preferred in the practice of this invention. The specificity of these tests follows from the fact that these hormones in a urine specimen can be sandwiched between the alpha-subunit-specific antibody, which has been immobilized on a plastic dipstick, and a beta specific antibody, such as beta hLH, which has been linked to the enzyme alkaline phosphatase. After unbound enzyme conjugate is removed by washing, the stick can be incubated in a substrate solution. The substrate reacts with the enzyme and deposits a blue end product on the reactive end of the stick. By way of example then, a semiquantitative analysis of hLH in urine can be made by comparing the intensity of the color on each stick with the color on the sticks incubated in, for example, concurrently run 0 m IU/ml, 20 m IU/ml and 40 m IU/ml calibrators. Color changes corresponding to response levels above one standard deviation, and more preferably those indicating response levels more than two standard deviations, above the base level of normal controls can be considered as an indication of a low level of fecundity.

EXAMPLE

Population and Methods

The herein disclosed clomiphene citrate challenge tests were utilized to prospectively assess future fertility potential in women greater than 35 years of age with unexplained fertility Baseline (day 2-3) and response levels (day 9-11) of follicle stimulating hormone (FSH), luteinizing hormone (LH), and 17-beta estradiol ($E_2$) were measured before and after administration of 100 mg clomiphene on days 5-9 of the menstrual cycle. Sixteen women had an exaggerated FSH response of over 26 mIU/ml or more (2 standard deviations (SD) above levels found in normal controls), which was considered a diminished ovarian reserve (DOR). Mean baseline FSH in 16 women in the DOR group was 13.5±5 SD mIU/ml with a response level of 38.9±13.8 mIU/ml, while the baseline in 30 women with adequate ovarian reserve (AOR) was 9±4.2 mIU/ml with a response level of 11.5±4.9 mIU/ml. There was a highly significant difference (p<0.0001) between FSH response levels of the two groups and between response to baseline levels in the DOR group. LH response was consistently greater than FSH response in the AOR group, while consistently less than FSH in the DOR group (p<0.001). One of 16 patients (6%) in the DOR group conceived; 14 of 30 (47%) conceived in the AOR group (p<0.005). These tests indicate that despite apparently "normal" ovulatory cycles, the DOR group has compromised follicular apparatus. Disparity between normal $E_2$ secretory capacity of the granulosa and diminished capacity to secrete inhibin could explain the inappropriately high FSH levels in response to the clomiphene citrate challenge test. Hence it would appear that this clomiphene challenge test can reliably predict fecundity irrespective of age. It can provide a prospective test of the reserves of the gonadal hypothalamic axis as an indicator of female fecundity.

The basic study to establish this invention was conducted upon fifty-one patients seeking counsel for infertility between June, 1983, and January, 1986. Criteria for inclusion were age of 35 years or above, regular menstrual periods (23-35 days), normal seminal fluid analysis of the partner, and no history suggestive of mechanical causes of infertility. All patients were followed until conception or up to 3.5 years. Within one year, if no pregnancy ensued, infertility workup was completed or re-evaluated. Four patients were found to suffer from multiple pelvic adhesions, and one husband had repeatedly subfertile semen analyses. These five were excluded from the statistical analysis of pregnancy.

The ovarian challenge test was based on the administration of clomiphene citrate (CC), 100 mg/day for five consecutive days, starting on day 5 of the menstrual cycle. Peripheral venous blood was drawn during the early (days 2-3) and late (days 9-11) follicular phase.

Hormone levels were measured by standard radioimmunoassay (RIA) for follicle stimulating hormone (FSH), luteinizing hormone (LH) (Amersham Radiochemical Center, Amersham, England, according to 2nd IRP human menopausal gonadotropin (HMG) reference standards), 17-B estradiol ($E_2$), progesterone and dehydroepianirosterone sulphate (DHEA-S) all by commercially available RIA kits. Hormone levels on cycle day 2 or 3 are referred to as the baseline hormonal profile, while days 9 to 11, are the preferred times to establish the response values.

An FSH response level higher than 26 mIU/ml, measured on days 9-11, was defined as an abnormal response and was designated as the diminished ovarian reserve (DOR) group. Patients whose response was within the normal range were defined as the adequate ovarian reserve (AOR) group. Twenty-six mIU/ml of FSH is more than two standard deviations above the mean value on days 9-11 as observed in 8 healthy volunteers aged 22-28 years, undergoing the same clomiphene challenge tests. The results of the clomiphene challenge tests were separately filed. Fertility promoting treatment was conducted irrespective of the clomiphene challenge test results or interpretation. Nearly all the women (90%) eventually had ovulation stimulation with gonadotropins. The one DOR patient who conceived did so during an IVF cycle subsequent to failures of human menopausal gonadotropin (hMG) treatment for 12 previous cycles. All values are expressed as mean ±standard deviation (SD). Statistical analysis was performed employing student's T test or the Fischer exact test as appropriate.

Results

Of the 51 women, 18 had an abnormal response to the clomiphene challenge tests; 33 had FSH response levels within 2 SD of mean normal values as defined above. Table 1 details the age, duration of infertility, duration of follow-up, gonadotropin treatment, and outcome in the 51 patients. The two groups of patients did not differ in age, duration of infertility, treatment, or mean follow-up, (see Table 1). Sixteen of 18 women in the DOR group (89%) and 31 of 33 in the AOR group were treated with hMG and human chorionic gonadotropin (hCG) for ovulation induction, performed according to individually adjusted schedules. During treatment and follow-up, only one of 18 women in the DOR group conceived (6.3%) while 14 of 33 (46.7%) conceived in the AOR group. The difference in conception rates is statistically significant (p <0.005). The results of these tests are summarized in Table I.

TABLE 1

PATIENT CHARACTERISTICS, TREATMENT AND OUTCOME ACCORDING TO OVARIAN RESERVE (VALUES ARE MEAN ± SD)

| | AGE (YEARS) | DURATION OF INFERTILITY (YEARS) | DURATION OF FOLLOW UP YEARS | AUGMENTATION OF OVULATION | | MID LUTEAL PROGESTERONE (NG/ML) | CONCEIVED | | FAILED TO CONCEIVE | |
|---|---|---|---|---|---|---|---|---|---|---|
| | | | | NO. | (%) | | NO. | (%) | NO. | (%) |
| Inadequate Ovarian Reserve | 40 ± 3.3 | 4.7 ± 3.9 | 2.0 ± 0.8 | 16 | (89) | 11.4 ± 3.4 | 1 | (6.3) | 15* | (93.5) |
| P Value | NS | NS | NS | NS | | <0.05 | <0.005 | | | |
| Adequate Ovarian Reserve | 39.6 ± 2.5 | 6.1 ± 4.3 | 1.6 ± 0.8 | 31 | (94) | 18.3 ± 3.4 | 14 | (46.7) | 16** | (53.3) |

*2 patients excluded because of probable tubal factors
**3 patients excluded because of probable tubal (2) or male (1) factors
NS Not statistically significant It should be noted that the baseline hormonal profiles differed only in respect to FSH levels. Although well within the normal range (13.5±5 mIU/ml), the mean FSH level was significantly higher (p<0.002) in the DOR group than in the AOR group. No other baseline values differed between the two groups. A highly significant increase in serum FSH levels was observed after clomiphene citrate administration in the DOR group (p<0.0001), while only moderate increase was detected in the AOR population (p=0.05). The difference between the two groups in response levels of FSH was highly significant (p<0.0001). In both groups a significant elevation in LH levels from baseline was documented, although LH levels on days 9-11 were significantly higher in the DOR group than in the AOR group ($p < 0.02$).

In 15 of 18 (83%) in the DOR group, FSH levels more than doubled, while in the AOR group only 3 of 33 (9%) had FSH levels twice as high after clomiphene citrate administration. This difference is statistically significant ($p < 0.0001$). In the DOR group a reversal of the ratio of the FSH/LH response was also noted in the same proportion of patients; in 15 of 18, FSH levels were higher than LH levels on days 9-11, while only 3 of 33 in the AOR group had higher FSH levels than LH levels ($p < 0.0001$). There was an obvious rise in $E_2$ after clomiphene citrate was administered in both groups, and higher levels were attained in the normal response group. However, none of the values differed significantly, probably because of the wide range of $E_2$ values.

P levels were less than 1 mg/ml in all but one patient sampled on days 2-3 and all but two patients sampled on days 9-11. Mean mid-luteal P levels are suggestive of ovulation in both groups: $11.4 \pm 3.4$ vs. $18.3 \pm 3.4$ mg/ml in the DOR and AOR groups respectively. However, peak luteal P levels were significantly higher in the AOR group ($p < 0.05$), see Table 1.

Despite a definite trend of elevation in delta-4A, T, and DHEA-S levels after clomiphene citrate challenge, no statistically significant differences were found between baseline lo and response levels, and no discrimination could be demonstrated on the basis of ovarian reserve Prolactin levels were somewhat lower after the clomiphene citrate challenge test, but the differences were not statistically significant.

Discussion

These results indicate that a diminished fertility potential can be detected through the utilization of a clomiphene citrate challenge test. This longitudinal study demonstrates that fecundity can be predicted on the basis of gonadotropin response to clomiphene citrate stimulation. The challenge test has a 93.5% sensitivity in recognizing the population with diminished fertility potential and a 47% specificity in identifying the fertile population. The specificity is apparently low; however, the 47% conception rate is remarkable in a relatively old group of apparently normal patients undergoing ovulation induction. It may be that older patients who have unexplained infertility have subtle ovulatory abnormalities. The favorable results of hMG/hCG augmentation of ovulation suggest that a hyperstimulated cycle may overcome those undefined abnormalities and can achieve pregnancy when the natural cycle have failed. The fact that all patients had normal baseline FSH and LH values and none had entered menopause during the follow-up period suggests that an inadequate ovarian reserve may be detected a considerable time before actual cessation of menses. During the early stages of perimenopause, there is a gradual rise in serum gonadotropins due to decreasing members of oocytes and follicles. The rise in FSH levels is earlier and more marked than LH levels. In contradistinction to the perimenopause, with clomiphene citrate adminstration during the reproductive span of life there is an early rise in pituitary gonadotropin levels which is more marked and sustained for LH than for FSH. In DOR patients, gonadotropin response to the clomiphene citrate challenge is reversed, being much more pronounced for FSH than LH. This peculiar response pattern of gonadotropins is similar to premenopausal FSH/LH ratio and may be attributed to a decrease in the ovarian elaboration of inhibin. Inhibin can specifically suppress plasma FSH levels, probably by reducing the release of FSH from adenohypophysis. Like steroidal hormones, inhibin is secreted by granulosa cells, whose secretory capacity is closely related to oocyte quality. A reduced capacity to secrete inhibin could explain the specific overshoot in FSH levels after the clomiphene citrate challenge. If that capacity is also related to oocyte quality, it may explain the severely compromised chances to conceive. Thus, a clomiphene citrate challenge may unmask incipient failure in an apparently normal follicular apparatus.

The increase in T and delta-4A following clomiphene citrate treatment is an established phenomenon. This increase in steroidogenesis is partly accounted for by the increase in LH levels which accelerate ovarian steroidogenesis. A direct action of clomiphene citrate on ovarian 3B-ol dehydrogenasedelta-5 isomerase is an additional route through which generation of delta-4A may increase. The elevated androgen levels during clomiphene citrate levels on days 9-11 were similar for the AOR and DOR groups; but this could not account for the significant difference in conception rates between the groups.

Hence this study shows that the herein disclosed clomiphene citrate challenge can be used as a stress test for the reserve of the ovarian-follicular apparatus. Therefore, it will prove helpful in clinical decisions regarding contraception, type and timing of profertility treatment, prognostication, and-above all-knowing when to abandon further efforts in an already over treated infertile woman whose failure to conceive remains unexplained.

From the above discussion, those skilled in this art will appreciate that although the application of clomiphene citrate for treatment of infertility and for testing the integrity of the hypothalamic-pituitary-ovarian axis is well established, it has not been described in the context of evaluating fecundity in patients seeking treatment for infertility. Those skilled in this art will also appreciated that the herein disclosed clomiphene challenge test also can be modified without departing from the limits and spirit of this patent disclosure. At the very least, the form of the clomiphene (e.g., administration via various salt forms), the days of testing and the administration dosage can be varied somewhat in the practice of the hereinafter claimed invention.

Thus having disclosed our invention we claim:

1. A method for predicting the fertility or infertility of a human female patient which comprises administering clomiphene to said patient during the period of days 2-9 of said patient's menstrual cycle, measuring the follicle stimulating hormone response level of said patient during the period of days 9-11 of said patient's menstrual cycle, and comparing said response level to normal response levels, wherein a response level significantly greater than normal response levels is predictive of infertility and a response level within normal response levels is predictive of fertility.

2. The method of claim 1 wherein a follicle stimulating hormone response level greater than two standard deviations above normal response levels is predictive of infertility.

3. The method of claim 1 wherein a follicle stimulating hormone response level greater than 26 mIU/ml is predictive of infertility.

4. The method of claim 1 wherein a follicle stimulating hormone response level of about 11.5±4.9 mIU/ml is predictive of fertility.

5. The method of claim 1 wherein the clomiphene is administered on days 5-9 of said patient's menstrual cycle.

6. The method of claim 5 wherein the clomiphene is administered in dosages of about 50 mg to about 150 mg per day.

7. The method of claim 6 wherein the clomiphene is administered in dosages of about 100 mg per day.

8. The method of claim 7 wherein the clomiphene is clomiphene citrate.

9. A method of predicting the fertility or infertility of a human female patient which comprises: determining a baseline level for follicle stimulating hormone in the period of days 2-3 of said patient's menstrual cycle;

administering clomiphene to said patient during the period of days 2-9 of said patient's menstrual cycle;

determining a response level of follicle stimulating hormone in the period of days 9-11 of said patient's menstrual cycle; and comparing said response level to said baseline level, wherein a response level significantly elevated over said baseline level is predictive of infertility.

10. The method of claim 9 wherein a response level more than double the baseline level is predictive of infertility.

11. The method of claim 9 wherein the clomiphene is administered on days 5-9 of said patient's menstrual cycle.

12. The method of claim 11 wherein the clomiphene is administered in dosages of about 50 mg to about 150 mg per day.

13. The method of claim 12 wherein the clomiphene is administered in dosages of about 100 mg per day.

14. The method of claim 13 wherein the clomiphene is clomiphene citrate.

15. A method of predicting the fertility or infertility of a human female patient which comprises administering clomiphene to said patient during the period of days 2-9 of said patient's menstrual cycle, measuring the luteinizing hormone response level of said patient during the period of days 9-11 of said patient's menstrual cycle, and comparing said response level to normal response levels, wherein a response level significantly greater than normal response levels is predictive of infertility.

16. The method of claim 15 wherein the clomiphene is administered in dosages of about 50 mg to about 150 mg per day on days 5-9 of said patient's menstrual cycle.

17. A method of predicting the fertility or infertility of a human female patient which comprises administering clomiphene to said patient during the period of days 2-9 of said patient's menstrual cycle, measuring the follicle stimulating hormone response level and the luteinizing hormone response level of said patient during the period of days 9-11 of said patient's menstrual cycle, and comparing said response levels, wherein a follicle stimulating hormone response level greater than the luteinizing hormone response level is predictive of infertility.

18. The method of claim 17 wherein the clomiphene is administered on days 5-9 of said patient's menstrual cycle.

19. The method of claim 18 wherein the clomiphene is administered in dosages of about 50 mg to about 150 mg per day.

20. The method of claim 19 wherein the clomiphene is administered in dosages of about 100 mg per day.

21. The method of claim 20 wherein the clomiphene is clomiphene citrate.

* * * * *